United States Patent [19]
Gertzman et al.

[11] Patent Number: 5,102,419
[45] Date of Patent: * Apr. 7, 1992

[54] ELASTOMERIC SURGICAL SUTURES COMPRISING SEGMENTED COPOLYETHER/ESTERS

[75] Inventors: Arthur A. Gertzman, Bridgewater; Mark T. Gaterud, Annandale, both of N.J.

[73] Assignee: Ethicon, Inc., Somerville, N.J.

[*] Notice: The portion of the term of this patent subsequent to May 29, 2007 has been disclaimed.

[21] Appl. No.: 129,426

[22] Filed: Nov. 25, 1987

Related U.S. Application Data

[63] Continuation of Ser. No. 338,407, Jan. 8, 1982, abandoned, which is a continuation of Ser. No. 77,055, Sep. 26, 1979, abandoned, which is a continuation-in-part of Ser. No. 967,656, Dec. 8, 1978, abandoned.

[51] Int. Cl.$^5$ .............................................. A61L 17/00
[52] U.S. Cl. ................................. 606/228; 264/210.1; 264/210.8
[58] Field of Search ...................... 606/228; 264/210.1, 264/210.8

[56] References Cited

U.S. PATENT DOCUMENTS

| | | | |
|---|---|---|---|
| 3,023,192 | 2/1962 | Shivers | 260/75 |
| 3,531,561 | 9/1970 | Trehu | 264/210 |

*Primary Examiner*—Robert J. Hill, Jr.
*Attorney, Agent, or Firm*—Robert L. Minier

[57] ABSTRACT

Elastomeric monofilament surgical sutures are characterized by the following combination of mechanical properties:

| | |
|---|---|
| Yield elongation | from about 2 to 9 percent |
| Visco-elastic elongation | from about 10 to 30 percent |
| Young's modulus | from about 30,000 to 200,000 psi |
| Tensile strength | at least about 40,000 psi |
| Knot strength | at least about 30,000 psi |

The sutures are soft and flexible with superior knot tying and knot security properties. The sutures may be prepared from selected elastomeric copolyether/ester polymers which may be melt extruded and drawn to obtain the desired fiber properties.

19 Claims, 1 Drawing Sheet

ELASTOMERIC SURGICAL SUTURES COMPRISING SEGMENTED COPOLYETHER/ESTERS

CROSS REFERENCE

This application is a continuation of application Ser. No. 338,407, filed Jan. 8, 1982, now abandoned, which is a continuation of application Ser. No. 077,055, filed Sept. 26, 1979, now abandoned, which is a continuation-in-part of application Ser. No. 967,656, filed Dec. 8, 1978, now abandoned.

BACKGROUND OF THE INVENTION

The present invention relates to surgical sutures, and more particularly, to soft, elastomeric sutures having unique handling and knot tying characteristics. The sutures may be prepared from segmented copolyether/esters or other elastomeric polymers.

Many natural and synthetic materials are presently used as surgical sutures. These materials may be used as single filament strands, i.e, monofilament sutures, or as multifilament strands in a braided, twisted or other multifilament construction. Natural materials such as silk, cotton, linen, and the like, of course do not lend themselves to the fabrication of monofilament sutures and are accordingly generally used in one of the multifilament constructions.

Synthetic materials which are extruded in continuous lengths can be used in monofilament form. Common synthetic monofilament sutures include polyethylene terephthalate, polypropylene, polyethylene, and nylon. Such monofilament sutures are preferred by surgeons for many surgical applications due to their inherent smoothness and noncapillarity to body fluids.

The presently available synthetic monofilament sutures all suffer to a greater or lesser degree from one particular disadvantage, that is inherent stiffness. Besides making the material more difficult to handle and use, suture stiffness can adversely affect knot tying ability and knot security. It is because of the inherent stiffness of available monofilament sutures that most larger suture sizes are braided or have other multifilament constructions with better handling flexibility.

Monofilament sutures of the prior art are also characterized by a low degree of elasticity, the most elastic of the above-mentioned synthetics being nylon which has a yield elongation of about 1.7 percent and a viscoelastic elongation of about 8.5 percent. The inelasticity of these sutures also makes knot tying more difficult and reduces knot security. In addition, the inelasticity prevents the suture from "giving" as a newly sutured wound swells, with the result that the suture may place the wound tissue under greater tension than is desirable, and may even cause some tearing, cutting or necrosis of the tissue.

The problems associated with the use of inelastic sutures in certain applications were recognized in U.S. Pat. No. 3,454,011, where it was proposed to fabricate a surgical suture composed of Spandex polyurethane. Such sutures, however, were highly elastic with "rubbery" characteristics and did not find general acceptance in the medical profession.

It is accordingly an object of the present invention to provide a novel soft, limp, monofilament suture material. It is a further object of this invention to provide a monofilament suture with a controlled degree of elasticity to accommodate changing wound conditions. It is another object of this invention to provide a new, nonabsorbable suture having a diameter of from about 0.01 to 1.0 mm and possessing unique and desirable physical properties. These and other objects will be made apparent from the ensuing description and claims.

SUMMARY

Monofilament sutures of the present invention are characterized by the following combination of physical properties:

| | |
|---|---|
| Yield elongation | from about 2 to 9 percent |
| Visco-elastic elongation | from about 10 to 30 percent |
| Young's modulus | from about 30,000 to 200,000 psi |
| Tensile strength | at least about 40,000 psi |
| Knot strength | at least about 30,000 psi |

Sutures possessing the above characteristics may be prepared by melt extruding certain elastomeric polymers such as copolyether/ester polymers to form a continuous filamentary strand, and thereafter drawing the extruded filament to obtain the desired suture properties. Certain copolyether/ester polymers available commercially from E. I. du Pont de Nemours & Co. under the tradename "HYTREL" have been discovered to be suitable starting materials for the preparation of sutures in accordance with the present invention.

Monofilament sutures having physical properties in accordance with the present invention are particularly useful in many surgical procedures where the suture is used to close a wound which may be subject to later swelling or change in position. The combination of low Young's modulus and significant yield elongation provides the suture with an appreciable degree of controlled elasticity under low applied force. As a result, the suture is able to "give" to accommodate swelling in the wound area. The relatively high visco-elastic yield elongation and high tensile strength of the suture allows the suture to stretch during knot tie-down so that the knot "snugs down" for improved tying ability and knot security with a more predictable and consistent knot geometry regardless of variations in suture tying technique or tension.

DESCRIPTION OF PREFERRED EMBODIMENTS

The sutures of the present invention are characterized by a combination of physical properties which are unique for monofilament sutures, and which provide the sutures of the present invention with unique and desirable functional properties.

Figure 1:
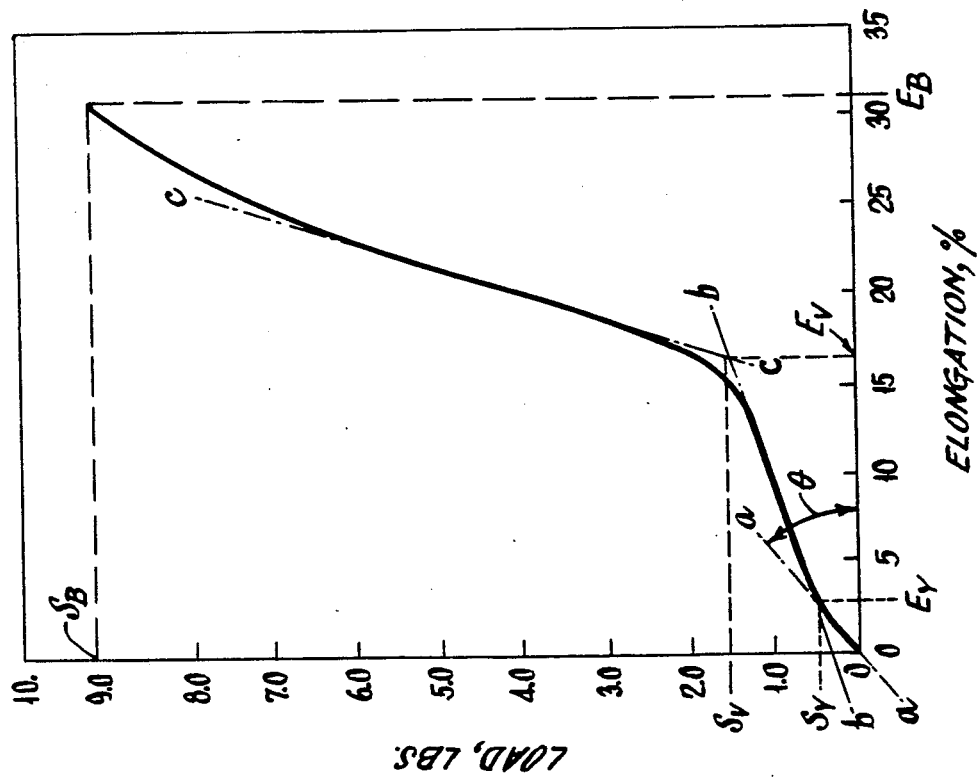
FIG. 1 is a representative stress-strain curve characteristic of the surgical filaments of the present invention.

The characteristic properties of the inventive sutures are readily determined by conventional test procedures. FIG. 1 illustrates a typical stress-strain or load-elongation diagram for the sutures of this invention. In FIG. 1, yield elongation (Ey) is the point at which permanent deformation of the suture begins to take place. So long as the filament is not elongated beyond Ey, elastic recovery is essentially complete. The sutures of the present invention have an Ey with the range of 2 to 9 percent.

Young's modulus is a measure of the slope of the stress-strain curve over the initial portion of the curve extending from the origin. In FIG. 1, line a is a drawn tangent to the curve at the origin, and Young's modulus is equal to tan $\theta$. The slope of the curve, and Young's modulus, are seen to be a measure of the resistance to elongation in the initial elastic portion of the curve. The sutures of the present invention are designed to have a significant, but relatively low modulus of 30,000 to 200,000 psi, and preferably within the range of 50,000 to 150,000 psi. A modulus within the claimed range provides the correct amount of increasing tension on the suture as the suture is extended toward its yield point (Ey). At lower values of Young's modulus, the suture readily elongates under very low tension to its yield point and the advantages of having a significant yield elongation are lost. At higher values of Young's modulus, filament stiffness becomes the controlling consideration, and the softness and good handling properties of the suture diminish.

The portion of the stress-strain curve extending between Ey and Ev on FIG. 1 is the visco-elastic region during which there is considerable elongation and permanent deformation of the suture with only slightly increasing tension. The visco-elastic elongation (Ev) of the sutures of the present invention is controlled to be within the range of from about 10 to 30 percent. This property of the suture allows the suture to draw down during knotting to assure good knot security.

As the suture is elongated beyond Ev, the load increases rapidly as indicated in FIG. 1. This rapid increase in load imparts a positive feel to the suture which, in the hands of a skilled surgeon, signals when Ev and maximum knot security are achieved. Preferably, the value of Ev is at least 2.5 times the value of Ey in order to provide the surgeon with a broad visco-elastic region in which to work during suture tie-down.

As seen in FIG. 1, the load from 0 to Ev elongation is relatively low compared to the breaking load (Sb). Preferably, the breaking load or straight tensile strength is at least 40,000 psi, and the load Sv corresponding to visco-elastic elongation is less than one-third of the breaking load, with the result that the suture may be easily knotted under relatively low forces and without risk of unintentionally breaking the suture. Knot strength of the suture is preferably at least 30,000 psi.

The breaking elongation (Eb) of the sutures of the present invention are generally within the range of 30 to 100 percent. Although this property is not critical to the performance of the suture since suture elongation in use does not generally exceed Ev, it is preferable that Eb be at least 1.5×Ev in order to reduce the possibility of inadvertently over elongating and breaking the suture during tie-down.

Figure 2:
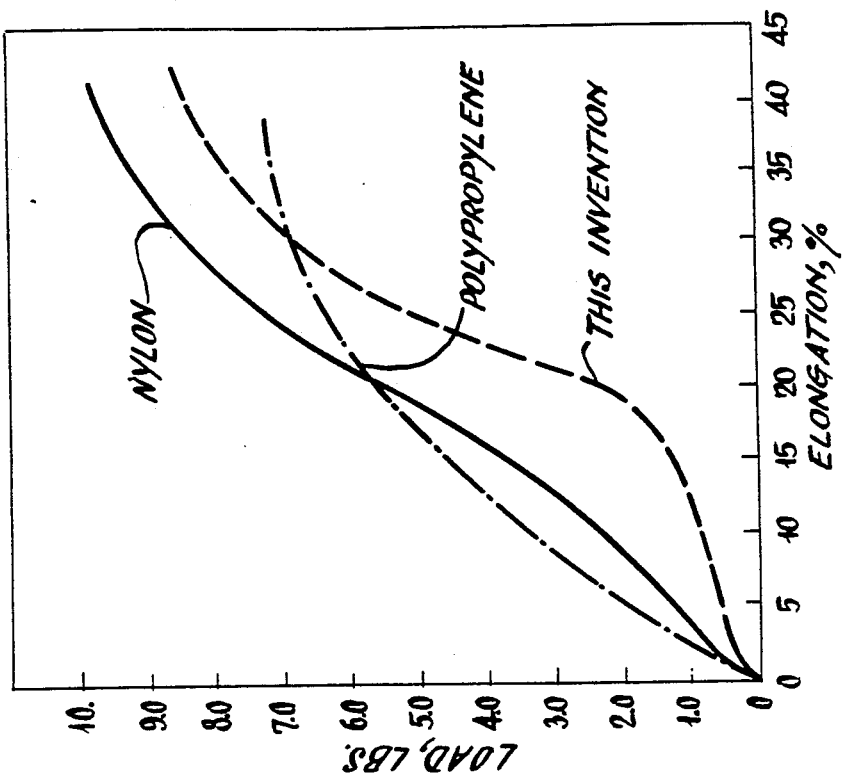
FIG. 2 is a representative stress-strain curve comparing filaments of the present invention with monofilament sutures of the prior art.

The unique mechanical properties of the sutures of the present invention will be more readily appreciated from FIG. 2 where such sutures are compared to nylon and polypropylene sutures of the prior art. Representative physical properties of these three suture materials are given in Table I. Each of these prior art sutures has a considerably higher Young's modulus which results in the characteristic stiffness of these materials. In addition, neither suture has a noticeable Ey or an extended viscoelastic region which characterize the sutures of the invention and impart the desirable properties discussed above.

The mechanical properties of the sutures of the present invention reflected in the relative values of Ev and Ey in combination with the low Young's modulus and high tensile strength are unique in the field of surgical sutures and distinguish the monofilament sutures of the present invention from all prior art materials.

TABLE I

| Suture property | Suture material | | |
|---|---|---|---|
| | Polypropylene | Nylon | This invention |
| Diameter, mils | 12.5 | 12.8 | 12.9 |
| (mm) | (0.32) | (0.33) | (0.33) |
| Tensile strength, psi | 58,900 | 75,200 | 64,700 |
| (Kg/cm$^2$) | (4,100) | (5,300) | (4,500) |
| Elongation to break, % | 32.2 | 40.1 | 39.5 |
| Visco-elastic elongation (Ev), % | 9.0 | 8.5 | 14.8 |
| Yield elongation (Ey), % | 1.1 | 1.7 | 2.2 |
| Stress at Ey (Sy), psi | 5,100 | 3,600 | 2,500 |
| (Kg/cm$^2$) | (360) | (250) | (180) |
| Stress at Ev (Sv), psi | 25,700 | 13,200 | 9,200 |
| (Kg/cm$^2$) | (1,800) | (930) | (650) |
| Young's modulus, psi | 425,000 | 221,000 | 112,000 |
| (Kg/cm$^2$) | (29,900) | (15,500) | (7,900) |

Sutures having mechanical properties in accordance with the present invention may be prepared from the segmented copolyether/ester compositions disclosed in U.S. Pat. No. 3,023,192, incorporated herein by reference, which states in part at Column 2, line 20 et seq.:

"The copolyetheresters of this invention are prepared by reacting one or more dicarboxylic acids or their ester-forming derivatives, one or more difunctional polyethers with the formula:

HO(RO)$_p$H (in which R is one or more divalent organic radicals and p is an integer of a value to provide a glycol with a molecular weight of between about 350 and about 6,000), and one or more dihydroxy-compounds selected from the class consisting of bis-phenols and lower aliphatic glycols with the formula:

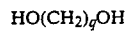

HO(CH$_2$)$_q$OH (in which q is 2-10), with the proviso that the reactants be selected so that substantially all of the repeating units of the polyester contain at least one aromatic ring. The resulting ester is then polymerized."

The preparation of other related segmented thermoplastic copolymers are described in the following additional references which are also incorporated herein by reference for their teachings in this regard: U.S. Pats. Nos. 3,651,014; 3,763,109; 3,766,146; and 3,784,520.

According to the above references, the disclosed segmented thermoplastic copolymers may be cast as films, injection molded to form objects, or melt extruded to form filaments. The products obtained in accordance with these references, however, are characterized by physical properties which are not desirable for surgical sutures. In particular, the filaments of the references are rubbery with a very high degree of elasticity as indicated by break elongations in excess of 500 percent. Tensile strengths, on the other hand, are very low, generally less than 8,000 psi. The filaments prepared from copolyether/esters in accordance with the teachings of these references therefore do not possess the mechanical properties of the sutures of the invention, and, in fact, are obviously not at all suitable for use as surgical sutures.

The disadvantages of the prior art references are overcome by means of the present invention wherein filaments extruded from certain copolyether/esters are quenched and drawn with the result that the mechanical properties of the filaments are controlled to be within the specific limits discovered to be particularly desirable for surgical sutures.

The segmented copolyether/esters useful in the present invention comprise a multiplicity of recurring long chain ether/ester units and short chain ester units joined head to tail through ester linkages according to the following general formula:

$$[(O-D-O-\overset{O}{\underset{\|}{C}}-R-\overset{O}{\underset{\|}{C}})_a(O-G-O-\overset{O}{\underset{\|}{C}}-R-\overset{O}{\underset{\|}{C}}-O)_b]_n \quad (I)$$

The long chain ether/ester units of the polymer are represented by the general formula:

$$-O-G-O-\overset{O}{\underset{\|}{C}}-R-\overset{O}{\underset{\|}{C}} \quad (II)$$

wherein G is a divalent radical remaining after the removal of terminal hydroxyl groups from a poly($C_{2\text{-}10}$ alkylene oxide)glycol having a molecular weight within the range of about 350 to 6,000, and R is a divalent radical remaining after the removal of carboxyl groups from an aromatic dicarboxylic acid having a molecular weight of less than about 300.

The short chain ester units are represented by the general formula:

$$-O-D-O-\overset{O}{\underset{\|}{C}}-R-\overset{O}{\underset{\|}{C}}- \quad (III)$$

wherein D is a divalent radical remaining after removal of hydroxyl groups from an alkyldiol having a molecular weight of less than about 250, and R is as defined above.

In the above Formula I, a is an integer such that the short chain copolymer segments represented by a comprise from 50 to 90 percent by weight of the total copolymer composition; b is an integer such that the long chain copolymer segments represented by b comprise from 10 to 50 percent of the total copolymer composition; and n is the degree of polymerization resulting in a fiberforming copolymer.

The copolyether/esters represented by Formula I may be melt extruded, quenched and drawn to obtain filaments having physical properties desirable for surgical sutures as above defined. Polymer to be extruded is dried at about 200–220° F. in a circulating hot air oven and/or under vacuum in order to remove all traces of moisture and other volatile materials. The polymer is then melt extruded and water quenched in accordance with the conventional melt spinning techniques for synthetic fibers. The fiber is finally drawn at least about 5X, and usually from about 7X to 9X to achieve molecular orientation.

The preparation of fibers useful as surgical sutures from copolyether/esters in accordance with the present invention is demonstrated by the following examples which are presented by way of illustration and are not limiting of the present invention. The polymers utilized in these examples are copolyether/esters prepared from 1,4-butanediol, dimethyl phthalate, and polytetramethylene ether glycol (M.W. of about 1,000), and are commercially available from E. I. du Pont de Nemours & Co. under the tradename "HYTREL". The polymer contains intrapolymerized butylenephthalate hard segments (short chain ester units) and polytetramethylene ether terephthalate soft segments (long chain ester units) and has the following general structure as reported in the Journal of Elastomers and Plastics 9, 416-38 (Oct., 1977):

$$[O-(CH_2)_4-O-\overset{O}{\underset{\|}{C}}-\underset{\text{(hard segment)}}{\underbrace{\bigcirc}}-\overset{O}{\underset{\|}{C}}]_a[O(CH_2CH_2CH_2CH_2O)_x-\overset{O}{\underset{\|}{C}}-\underset{\text{(soft segment)}}{\underbrace{\bigcirc}}-\overset{O}{\underset{\|}{C}}]_b \quad (IV)$$

wherein a and b are as defined above and x is an integer reflecting the molecular weight of the ether glycol reactant (x=14 for M.W. of about 1,000).

In the following examples, physical properties of individual monofilaments were determined on an Instron tensile tester under the following conditions:

| | |
|---|---|
| Crosshead speed (XH): | 5 in/min |
| Chart speed (CS): | 10 in/min |
| Sample length (GL): | 5 in |
| Scale load (SL): | 2 lbs/in |

With reference to FIG. 1, Young's modulus is calculated from the slope a of the stress-strain curve in the initial linear, elastic region as follows:

$$\text{Young's modulus (psi)} = \frac{\tan \theta \times GL \times CS \times SL}{XH \times XS}$$

wherein
$\theta$ = the angle indicated in FIG. 1
XS = the cross-sectional area of the fiber, in$^2$ SL, XH, CS, and GL are as identified above.

Yield stress (Sy) is the load at the point of intersection of lines a and b drawn tangent to the initial elastic region and the visco-elastic region, respectively, of the curve as illustrated in FIG. 1. Yield elongation (Ey) is the elongation corresponding to Sy and is read directly off the stress-strain curve.

Visco-elastic stress (Sv) is the load at the point of intersection of line b with line c drawn tangent to the curve as illustrated in FIG. 1. Visco-elastic elongation (Ev) is the elongation corresponding to Sv and is read directly off the curve.

Break elongation (Eb) and breaking tensile strength (Sb) are read directly off the stress-strain curve as illustrated in FIG. 1.

EXAMPLE I

A sample of copolyether/ester of Formula IV having approximately 40 wt percent soft segments and comprising approximately 51 percent terephthaloyl units, 16 percent units derived from polytetramethylene ether glycol, and 33 percent units derived from 1,4-butanediol was dried four hours at 200° F. in a circulating hot air oven and then further dried under vacuum at 100 microns (no heat) for 16 hours. The dry polymer was placed in a one-inch horizontal extruder and extruded through a J/50/1 die at an extrusion temperature of 380° F.

The extrudate was quenched in water at ambient temperature and drawn to a size 2-0 monofilament suture using a 8.8X draw ratio at a temperature of 530° F. and with a take-up speed of 485 ft/min. Physical properties of the resulting filaments are given in Table II.

EXAMPLE II

A sample of copolyether/ester of Formula IV having approximately 23 wt percents of segments and comprising approximately 45 percent terephthaloyl units, 4 percent orthophthaloyl units, 20 percent units derived from polytetramethylene ether glycol and 31 percent units derived from 1,4-butanediol was dried and extruded at 400° F. as described in Example I. The extrudate was quenched and drawn into a size 2-0 monofilament using a 7.5X draw ratio at a temperature of 450° F. and with a take-up speed of 412 ft/min. Physical properties of the resulting filaments are given in Table II.

EXAMPLE III

A sample of copolyether/ester of Formula IV having approximately 18 wt percent soft segments and comprising approximately 41 percent terephthaloyl units, 35 percent units derived from polytetramethylene ether glycol and 24 percent units derived from 1,4-butanediol was dried and extruded at 405° F. as described in Example I. The extrudate was quenched and drawn into a size 2-0 monofilament suture using a 6.5 draw ratio at a temperature of 560° F. The take-up speed was 75 ft/min. Physical properties of the resulting filaments are given in Table II. It is noted that the Young's modulus of these filaments exceeded the maximum desirable limit for sutures of the present invention.

EXAMPLE IV

Three parts of a copolyether/ester of Example I and two parts of a copolyether/ester of Example III were dry blended to provide a polymer having a total of 30.2 percent soft segments. The blended material was dried in a vacuum oven for two hours at 1-2 mm Hg (no heat), and then heated at 50° C. for three hours at 1-2 mm Hg.

The dried mixture was melt blended in a ⅜-inch Brabender extruder with a 25-inch barrel with a 20/1 screw and extruded at 430° F. through a 5/32-inch die in a vertical monofilament assembly. The extrudate was water quenched at ambient temperature, pelletized, and again dried as described above for the dry-blended material before extruding into monofilament sutures. A size 2-0 monofilament suture of this material was extruded at 400° F. using a 7.9X draw ratio at a temperature of 460° F. and a take-up speed of 435 ft/min. Physical properties of the resulting filaments are given in Table II.

EXAMPLE V 3.5 Parts of a copolyether/ester of Example I and 1.5 parts of a copolyether/ester of Example III were dry-blended for a total of 33.4 percent soft segments and extruded following the general procedure of Example IV, and using a final draw ratio of 7.5X with a draw temperature of 485° F. and a take-up speed of 412 ft/min to obtain a size 2-0 monofilament suture. The physical properties of the resulting filaments are given in Table II.

EXAMPLE VI

The procedure of Example IV was repeated using various blends of copolyether/ester polymers of Examples I, II and III having the compositions and blended in ratios as shown in Table II. The physical properties of the resulting filaments are also given in Table III.

EXAMPLE VII

A copolyether/ester of Example I with 40 wt percent soft segments was dried and extruded in accordance with the general procedure of Example I using a 20 mil spinnerette to obtain a size 5-0 suture, and a 50 mil spinnerette to obtain a size 0 suture. Drawing conditions and physical properties of the resulting suture are compared in Table IV with a size 2-0 suture of the same composition prepared according to Example I.

TABLE II

| | Examples | | | | |
|---|---|---|---|---|---|
| | I | II | III | IV | V |
| Suture size | 2-0 | 2-0 | 2-0 | 2-0 | 2-0 |
| Diameter, mils | 11.1 | 13.1 | 12.2 | 13.2 | 13.2 |
| (mm) | (0.28) | (0.33) | (0.31) | (0.34) | (0.34) |
| Knot strength, psi | 37,200 | 39,700 | 44,900 | 40,100 | 41,000 |
| (Kg/cm$^2$) | (2,600) | (2,780) | (3,140) | (2,800) | (2,870) |
| Tensile strength, psi | 64,100 | 71,300 | 72,300 | 65,500 | 60,500 |
| (Kg/cm$^2$) | (4,490) | (4,990) | (5,060) | (4,580) | (4,200) |
| Break elongation, % | 31.8 | 27.8 | 18.3 | 25.2 | 31.4 |
| Visco-elastic elongation, % | 18.6 | 13.3 | 7.25 | 10.35 | 11.6 |
| Yield elongation, % | 3.2 | 2.9 | 2.6 | 4.2 | 4.7 |
| Young's modulus, psi | 50,000 | 172,000 | 320,000 | 140,000 | 120,000 |
| (Kg/cm$^2$) | (3,500) | (12,000) | (22,400) | (9,800) | (8,400) |

TABLE III

| Polymer compositions | | Wt % soft segments in blend | Young's modulus psi (Kg/cm$^2$) | Break elongation Eb, % | Visco-elastic elongation Ev, % | Yield elongation Ey, % |
|---|---|---|---|---|---|---|
| Wt % soft segments of components | Wt ratio of components | | | | | |
| 40/23 | 65/35 | 34.05 | 84,000 | 34.8 | 14.3 | 9.2 |

TABLE III-continued

| Polymer compositions | | Wt % soft segments in blend | Young's modulus psi (Kg/cm²) | Break elongation Eb, % | Visco-elastic elongation Ev, % | Yield elongation Ey, % |
|---|---|---|---|---|---|---|
| Wt % soft segments of components | Wt ratio of components | | | | | |
| 40/18 | 75/25 | 34.50 | 107,000 (7,470) (5,850) | 33.4 | 13.3 | 3.2 |
| 40/23 | 50/50 | 31.50 | 105,000 (7,320) | 33.7 | 14.7 | 1.9 |
| 40/18 | 70/30 | 33.40 | 120,000 (8,390) | 31.4 | 11.6 | 4.7 |
| 40/18 | 65/35 | 32.30 | 134,000 (9,400) | 27.5 | 12.1 | 4.6 |
| 40/18 | 60/40 | 31.20 | 140,000 (9,790) | 26.5 | 10.2 | 4.8 |
| 40/18 | 55/45 | 30.10 | 170,000 (11,920) | 24.5 | 10.8 | 2.6 |
| 40/18/23 | 30/30/40 | 26.60 | 173,000 (12,080) | 18.9 | 10.3 | 3.5 |
| 40/23/18 | 30/30/40 | 26.10 | 201,000 (14,060) | 22.4 | 10.3 | 2.8 |

TABLE IV

| | Suture size | | |
|---|---|---|---|
| | 5-0 | 2-0 | 0 |
| Draw ratio | 7.5 | 8.8 | 7.3* |
| Draw temperature, °F. | 340 | 530 | 370 |
| Take-up, ft/min | 205 | 485 | 110 |
| Diameter, mils | 7.08 | 11.10 | 14.03 |
| Knot strength, psi (Kg/cm²) | 48,600 (3,400) | 37,200 (2,600) | 34,200 (2,400) |
| Tensile strength, psi (Kg/cm²) | 67,500 (4,700) | 64,100 (4,400) | 68,600 (4,800) |
| Break elongation, % | 43.5 | 31.8 | 36.7 |
| Visco-elastic elongation, % | 10.8 | 18.6 | 17.6 |
| Yield elongation, % | 3.0 | 3.2 | 6.3 |
| Young's modulus, psi (Kg/cm²) | 49,000 (3,400) | 50,000 (3,500) | 51,000 (3,600) |

*Two stage draw

EXAMPLE VIII

Monofilament sutures prepared from a copolyether/ester of Example II with 23 wt percent soft segments were sterilized by cobalt-60 irradiation and with ethylene oxide in accordance with conventional procedures for sterilizing surgical sutures. The physical properties of the sutures were affected only slightly by ethylene oxide sterilization, and even less by cobalt-60, as shown by the data in Table V.

TABLE V

| Suture | Nonsterile control | Sterilized | |
|---|---|---|---|
| | | Co⁶⁰ | E.O. |
| Diameter, mils | 12.5 | 12.6 | 13.2 |
| Knot strength, psi (Kg/cm²) | 35,300 (2,500) | 33,400 (2,300) | 29,900 (2,100) |
| Tensile strength, psi (Kg/cm²) | 70,300 (4,900) | 70,000 (4,900) | 67,700 (4,800) |
| Break elongation, % | 28.2 | 31.6 | 45.2 |
| Visco-elastic elongation, % | 13.2 | 15.0 | 23.5 |
| Yield elongation, % | 2.9 | 2.3 | 2.2 |
| Young's modulus, psi (Kg/cm²) | 185,000 (13,000) | 165,000 (11,600) | 138,000 (9,600) |

The important physical properties of the sutures prepared from copolyether/esters are responsive to changes in polymer composition and processing conditions. For example, visco-elastic elongation and yield elongation increase as the proportion of soft segments in polymer are increased, and conversely, Young's modulus decreases with an increasing proportion of soft segments. The break elongation may be decreased and tensile strength increased by employing higher draw ratios during the manufacture of the suture. By regulation of the composition and processing variables therefor, it is possible to obtain specific mechanical properties for individual sutures with a great degree of latitude.

While the preceding examples have been directed to the preparation of monofilament sutures of copolyether/esters, this was for the sake of convenience in describing one polymer system and the effect of various polymer compositions and spinning conditions on fiber properties. The copolyether/ester polymers may also be used in the manufacture of braided or other multifilament suture constructions, and single filaments and braids may be used in the preparation of surgical fabrics and knitted or woven prosthetic devices such as vein and arterial grafts. In addition, elastomeric filaments having a combination of physical properties in accordance with the present invention may be prepared from other polymer systems such as polyurethane or silicone elastomers or polyether copolymers of urethane or silicone elastomers. Furthermore, elastomeric filaments of the present invention may be blended with each other, with other elastomeric or nonelastomeric filaments, and with either absorbable or nonabsorbable filaments in order to provide yarns and fabrics with special properties, all of which is deemed to be included within the scope of the present invention.

What is claimed is:

1. A nonabsorbable elastomeric surgical suture in a sterile condition comprising a drawn and oriented monofilament of a segmented copolyether/ester polymer having the following combination of mechanical properties:

| | |
|---|---|
| Yield elongation | from about 2 to 9 percent |
| Visco-elastic elongation | from about 10 to 30 percent |
| Young's modulus | from about 30,000 to 200,000 psi |
| Tensile strength | at least about 40,000 psi |
| Knot strength | at least about 30,000 psi |

2. A method of closing a wound by approximating and securing the wound tissue with a nonabsorbable elastomeric surgical suture in a sterile condition comprising a monofilament having the following combination of mechanical properties:

| Yield elongation | from about 2 to 9 percent |
| --- | --- |
| Visco-elastic elongation | from about 10 to 30 percent |
| Young's modulus | from about 30,000 to 200,000 psi |
| Tensile strength | at least about 40,000 psi |
| Knot strength | at least about 30,000 psi |

3. A drawn and oriented elastomeric surgical filament in a sterile condition comprising a segmented copolyether/ester consisting essentially of a multiplicity of recurring long chain ether/ester units and short chain ester units joined head to tail through ester linkages and having the following general formula:

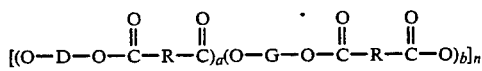

wherein G is a divalent radical remaining after the removal of terminal hydroxyl groups from a poly($C_{2-10}$ alkylene oxide) glycol having a molecular weight of about 350 to 6,000; R is a divalent radical remaining after removal of carboxyl groups from an aromatic dicarboxylic acid having a molecular weight less than about 300; and D is a divalent radical remaining after removal of hydroxyl groups from an alkyldiol having a molecular weight less than about 250; a and b are integers such that the short chain untis represented by a comprise from 50 to 90 percent by weight of the composition; and n is the degree of polymerization resulting in a fiber-forming polymer, said drawn filaments being characterized by the following physical properties:

| Tensile strength | at least about 40,000 psi |
| --- | --- |
| Knot strength | at least about 30,000 psi |
| Yield elongation | from about 2 to 9 percent |
| Visco-elastic elongation | from about 10 to 30 percent |
| Young's modulus | from about 30,000 to 200,000 psi |

4. A drawn and oriented elastomeric, nonabsorbable surgical filament in a sterile condition comprising a segmented copolyether/ester consisting essentially of a multiplicity of recurring long chain ether/ester units and short chain ester units joined head to tail through ester linkages and having the following general formula:

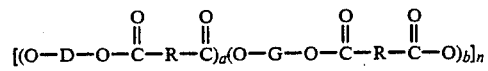

wherein G is a divalent radical remaining after the removal of terminal hydroxyl groups from a poly($C_{2-10}$ alkyleneoxide)glycol having a molecular weight of about 350 to 6,000; R is a divalent radical remaining after removal of carboxyl groups from an aromatic dicarboxylic acid having a molecular weight less than about 300; and D is a divalent radical remaining after removal of hydroxyl groups from an alkyldiol having a molecular weight less than about 250; a and b are integers such that the short chain units represented by a comprise from 50 to 90 percent by weight of the composition; and n is the degree of polymerization resulting in a fiber-forming polymer, said drawn filaments being characterized by the following physical properties:

| Tensile strength | at least about 40,000 psi |
| --- | --- |
| Knot strength | at least about 30,000 psi |
| Yield elongation | from about 2 to 9 percent |
| Visco-elastic elongation | from about 10 to 30 percent |
| Young's modulus | from about 30,000 to 200,000 psi. |

5. A filament of claim 4 wherein the Young's modulus is from 50,000 to 150,000, the tensile stress at the visco-elastic elongation yield point is less than about one-third the suture tensile strength, the elongation to break is about 30 to 100 percent and is at least 1.5 times the visco-elastic elongation and the visco-elastic elongation is at least 2.5 times the yield elongation.

6. A method of closing a wound by approximating and securing the wound tissue with a surgical fiber of claims 3 or 4.

7. A filament of claims 3 or 4 wherein G is derived from poly(tetramethyleneoxide)glycol, D is derived from 1,4-butanediol, and R is derived from a phthalic acid.

8. A filament of claim 7 wherein R is selected from the group consisting of terephthaloyl, isophthaloyl, orthophthaloyl, and mixtures thereof.

9. A filament of claim 7 wherein said poly(tetramethyleneoxide)glycol has a molecular weight of about 1,000.

10. A filament of claim 9 comprising a mixture of individual segmented copolyether/ester polymers having from about 18 to 40 percent by weight long chain ether/ester units wherein said mixture contains an average of from about 26 to 35 percent long chain ether/ester units.

11. A filament of claim 10 wherein said polymer mixture comprises from about 55 to 75 percent by weight of polymer having about 40 percent short chain ester units, and from about 25 to 45 percent by weight of polymer having about 18 percent short chain ester units.

12. A filament of claim 10 wherein said polymer mixture comprises approximately 40 percent by weight of a polymer having about 40 percent long chain ether/ester units, from about 30 to 40 percent by weight of a polymer having about 23 percent long chain ether/ester units, and from about 30 to 40 percent by weight of a polymer having about 18 percent long chain ether/ester units.

13. A filament of claim 7 wherein the long chain units represented by b comprise about 40 wt percent of the copolyether/ester.

14. A filament of claim 13 comprising approximately 51 percent terephthaloyl units, 16 percent units derived from polytetramethylene ether glycol, and 33 percent units derived from 1,4-butanediol.

15. A filament of claim 14 characterized by a visco-elastic elongation of about 19 percent and a Young's modulus of about 50,000 psi.

16. A filament of claim 7 wherein the long chain units represented by b comprise about 23 wt percent of the copolyether/ester.

17. A filament of claim 16 comprising approximately 45 percent terephthaloyl units, 4 percent orthophthaloyl units, 20 percent units derived form polytetramethylene ether glycol and 31 percent units derived from 1,4-butanediol.

18. A filament of claim 17 characterized by a visco-elastic elongation of about 13 percent and a Young's modulus of about 170,000 psi.

19. A method of closing a wound by approximating and securing the wound tissue with a surgical fiber of claim 7.

* * * * *

UNITED STATES PATENT AND TRADEMARK OFFICE
CERTIFICATE OF CORRECTION

PATENT NO. : 5,102,419

DATED : April 7, 1992

INVENTOR(S) : Gertzman et al.

It is certified that error appears in the above-identified patent and that said Letters Patent is hereby corrected as shown below:

Cover page     delete the disclaimer item designated by an asterisk "[*]" and the designation "Notice:" in its entirety.

Signed and Sealed this

Twenty-first Day of September, 1993

Attest:

BRUCE LEHMAN

Attesting Officer     Commissioner of Patents and Trademarks